United States Patent [19]
de Ledinghen

[11] Patent Number: 5,952,879
[45] Date of Patent: Sep. 14, 1999

[54] DEVICE FOR THE SIMULTANEOUS DEMODULATION OF A MULTIFREQUENCY SIGNAL, PARTICULARLY FOR AN EDDY CURRENT MEASUREMENT

[75] Inventor: Edouard de Ledinghen, Paris, France

[73] Assignee: Intercontrole, Rungis Cedex, France

[21] Appl. No.: 08/981,377

[22] PCT Filed: Jun. 19, 1996

[86] PCT No.: PCT/FR96/00947

§ 371 Date: Dec. 18, 1997

§ 102(e) Date: Dec. 18, 1997

[87] PCT Pub. No.: WO97/01217

PCT Pub. Date: Jan. 9, 1997

[30] Foreign Application Priority Data

Jun. 20, 1995 [FR] France ................................ 9507357

[51] Int. Cl.[6] .............................. H03D 3/00; H04L 27/22
[52] U.S. Cl. ......................... 329/304; 329/306; 375/324; 375/329
[58] Field of Search ..................... 329/304–310; 375/324, 325, 328, 329–333

[56] References Cited

U.S. PATENT DOCUMENTS

| | | |
|---|---|---|
| 4,303,885 | 12/1981 | Davis et al. . |
| 4,467,281 | 8/1984 | Davis et al. . |
| 5,805,642 | 9/1998 | Wei et al. ............................ 329/304 X |

FOREIGN PATENT DOCUMENTS

| | | |
|---|---|---|
| 3435032 A1 | 4/1986 | Germany . |
| WO 90/04292 | 4/1990 | WIPO . |

*Primary Examiner*—David Mis
*Attorney, Agent, or Firm*—Pearne, Gordon, McCoy & Granger LLP

[57] ABSTRACT

A device for the simultaneous demodulation of a multifrequency signal comprising a processor in which demodulation takes place by calculation. An injector's output signal is multiplied by a complex signal having sinusoids of varying frequencies corresponding to frequency-shifted carriers, thereby transposing the injector's signal on intermediate frequencies.

3 Claims, 2 Drawing Sheets

DEVICE FOR THE SIMULTANEOUS DEMODULATION OF A MULTIFREQUENCY SIGNAL, PARTICULARLY FOR AN EDDY CURRENT MEASUREMENT

DESCRIPTION

1. Technical Field

The present invention relates to a device for the simultaneous demodulation of a multifrequency signal, particularly for a measurement by eddy currents.

2. Prior Art

The mimic diagram of an eddy current measuring apparatus, illustrated in FIG. 1, comprises a balancing oscillator 10, an injector 11 and a demodulator 12 supplying a digital output SN.

The oscillator has the function of producing a multifrequency signal on the basis of a sum of 1 to N pure sinusoids. The function of the balancer is to reduce the influence of carriers in order to relatively amplify the modulating signal (eddy current signal). The function of the injector 11 is to supply a sensor 13 in which the eddy current modulation takes place. The function of the demodulator 12 is to extract the modulating signal (eddy current modulation) from the carriers used.

In such an apparatus, the technical data are generally as follows:
- the sinusoidal carriers have a frequency between 1 kHz and 4 MHz;
- a measuring apparatus currently uses between one and four carriers simultaneously;
- The pass band of the eddy current signals does not exceed 1 kHz;
- the eddy current modulation is a complex modulation: amplitude and phase;
- the function of the demodulator is to extract these two informations for each of the carriers and extracts in cartesian form the signal modulated in the sensor having the following equation: Xcos(wt)+Ysin(wt). The demodulator extracting X and Y.

Existing apparatuses inter alia use two demodulation methods.

Synchronous sinusoidal demodulation

The mimic diagram used is shown in FIG. 2.

The signal coming from the injector 11 is distributed in two identical channels. In one it is multiplied by a pure sinusoid S1 at the frequency of one of the carriers used. In the other it is multiplied by a sinusoidal signal S2 at the same frequency, but in phase quadrature with the first. The result of these multiplications has the effect of transposing the signal of the injector in base band. A low-pass filtering (filters 20, 21) at the maximum frequency of the eddy currents (e.g. fc=500 Hz) makes it possible to extract the pairs X,Y.

This demodulation method makes it necessary to reproduce the diagram of FIG. 2 with the same number of copies as there are simultaneously used frequencies: f1, f2, fn, where signals S1 and S2 have frequency f1, signals S1' and S2' have frequency f2, and so forth, as shown in FIG. 3.

Demodulation by quadrature sampling

This method uses the mimic diagram illustrated in FIG. 4.

The signal coming from the injector 11 is distributed on two identical channels. On one, it is connected to the filter 20 for a brief instant of the period of the sinusoid of the carrier which it is wished to demodulate. For the remainder of the time, the thus sampled voltage is maintained at the input of the filter. On the other channel, sampling takes place at the same frequency, but with a 90° phase shift (in quadrature).

In the same way as hereinbefore, this demodulation method makes it necessary to reproduce the mimic diagram illustrated in FIG. 4 with the same number of copies as there are simultaneously used frequencies. It also fails to efficiently reject any harmonics of the carrier signal.

DESCRIPTION OF THE INVENTION

The invention relates to a device for the simultaneous demodulation of a multifrequency signal, which comprise a processor in which demodulation takes place by calculation. Advantageously, said device comprises an injector, whose output signal is multiplied by a complex signal, which can have the following form:

$$S3 = a_1\sin\{2\pi(f_1 + \varepsilon_1)t + \varphi_1\} + a_2\sin\{2\pi(f_2 + \varepsilon_2)t + \varphi_2\} + \ldots a_n\sin\{2\pi(f_n + \varepsilon_n)t + \varphi_n\}$$

$\epsilon_1$ being a small frequency deviation and $\alpha_1$ a phase, the frequencies of the N sinusoids being the frequencies of the frequency-shifted carriers, so as to transpose the signal of the injection on the intermediate frequencies.

Advantageously, the device comprises an injector followed by a multiplier and a low-pass filter. This filter, having an antialiasing function, is followed by a digital converter.

Advantageously, said device can be used for a measurement by eddy currents.

DETAILED DESCRIPTION OF EMBODIMENTS

Figure 5:
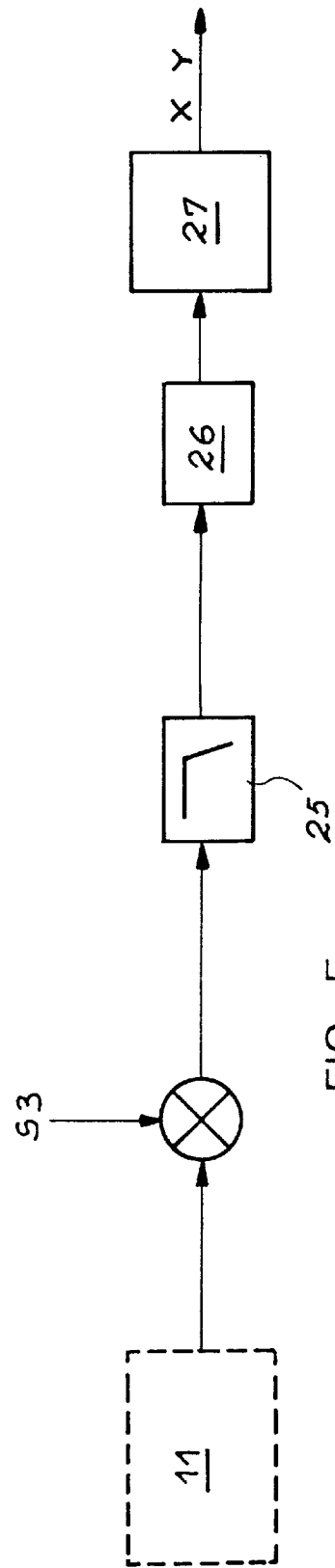
FIG. 5 shows a demodulation device for illustrating the process according to the invention.
Figure 1:
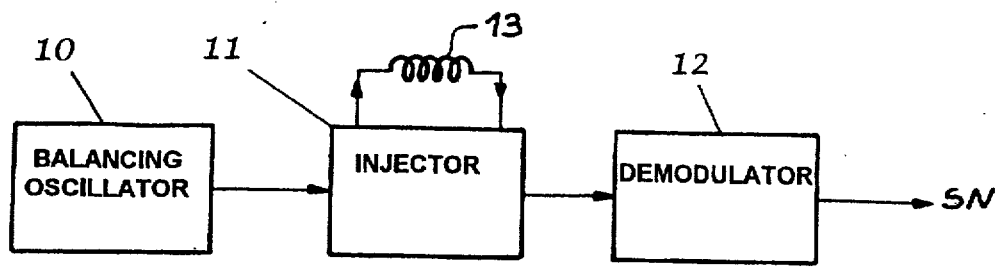
Figure 2:
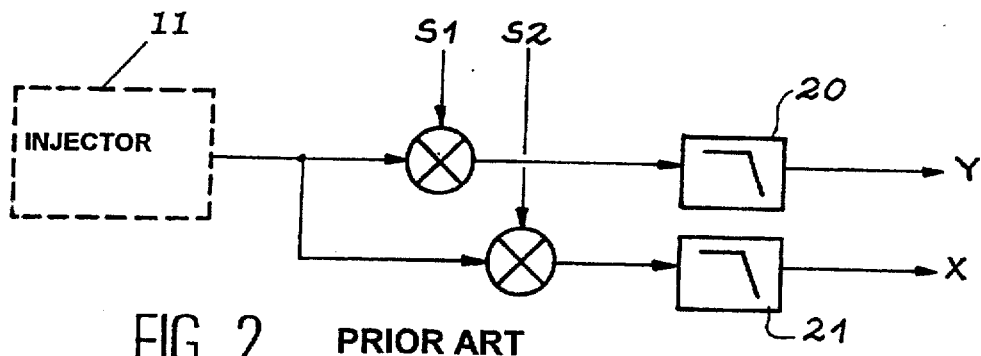
Figure 3:
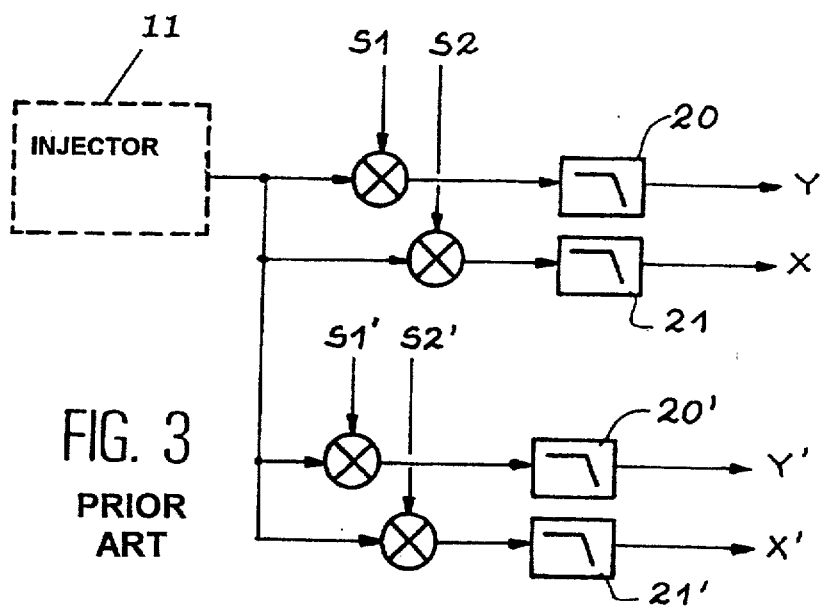
Figure 4:
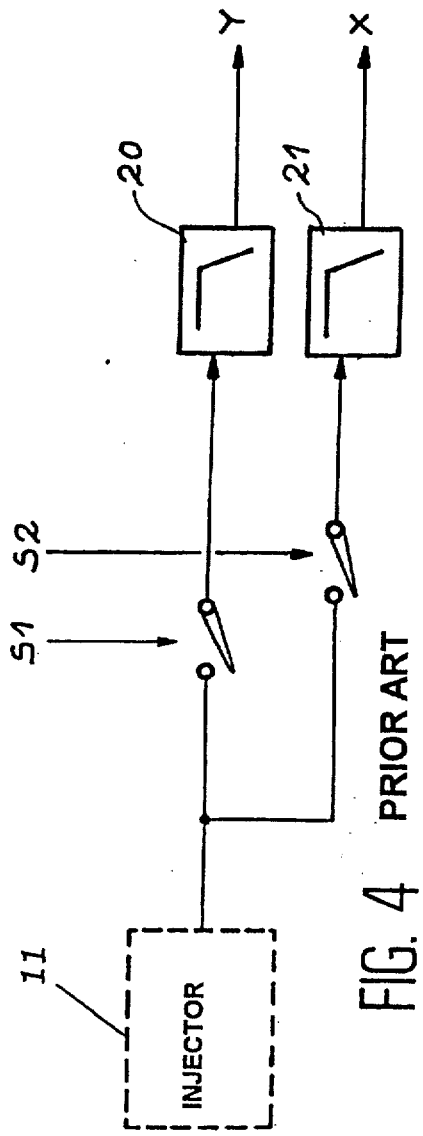
Figure 5:
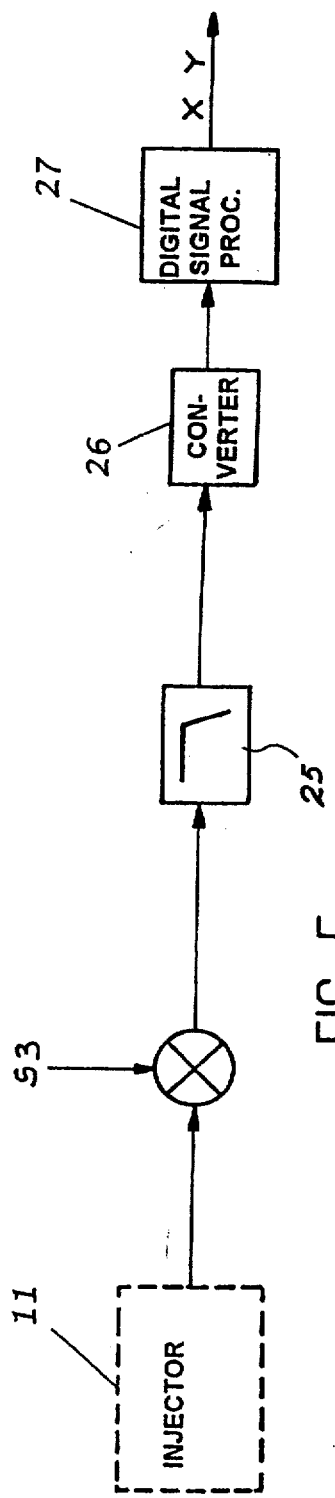

The invention relates to a process for the demodulation of a multifrequency signal, which is the sum of several amplitude and phase-modulated carrier waves. As illustrated in FIG. 5, the signal coming from the injector is multiplied by a complex signal formed from several elementary signals, for example:

$$S3 = a_1\sin\{2\pi(f_1 + \varepsilon_1)t + \varphi_1\} + a_2\sin\{2\pi(f_2 + \varepsilon_1)t + \varphi_2\} + \ldots a_n\sin\{2\pi(f_n + \varepsilon_n)t + \varphi_n\}$$

If N carriers are simultaneously used, the signal used for the multiplication is the sum of N sinusoids. The frequencies of the N sinusoids are the N frequencies of the carriers, frequency-shifted by e.g. a few kHz. For example, if use is simultaneously made of the carriers 100, 240 and 500 kHz, the signal is multiplied by 101, 242.5 and 505 kHz (said values being given in exemplified manner and are not exclusive).

This product has the effect of transposing the signal of the injection 11 on intermediate frequencies. These intermediate frequencies are the respective differences between the frequency of the carrier signal and the frequency of the operand. In the above example, said intermediate frequencies are 1, 2.5 and 5 kHz.

The following low-pass filter 25 (fc=10 kHz) fulfils the antialiasing function prior to the digital conversion of the signal (converter 26) on 16 bits at approximately 20 kHz (all values nonexclusive).

The digital signal processor 27 has the function of performing the actual demodulation, i.e. transposing the signal in base band. Any digital demodulation method can be used.

Figure 1:
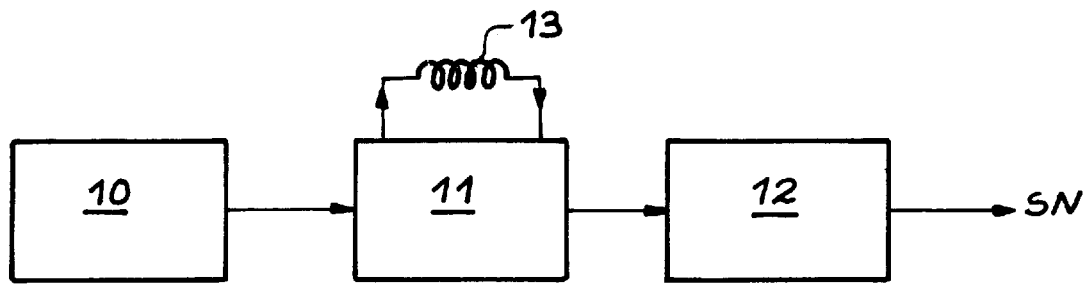
FIG. 1 shows a prior art, eddy current measuring apparatus.
Figure 2:
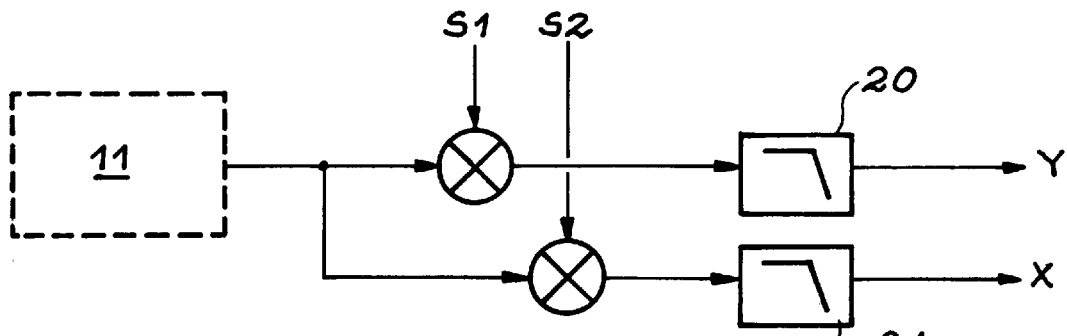
FIGS. 2 and 3 illustrate prior art, synchronous, sinusoidal demodulation devices.
Figure 3:
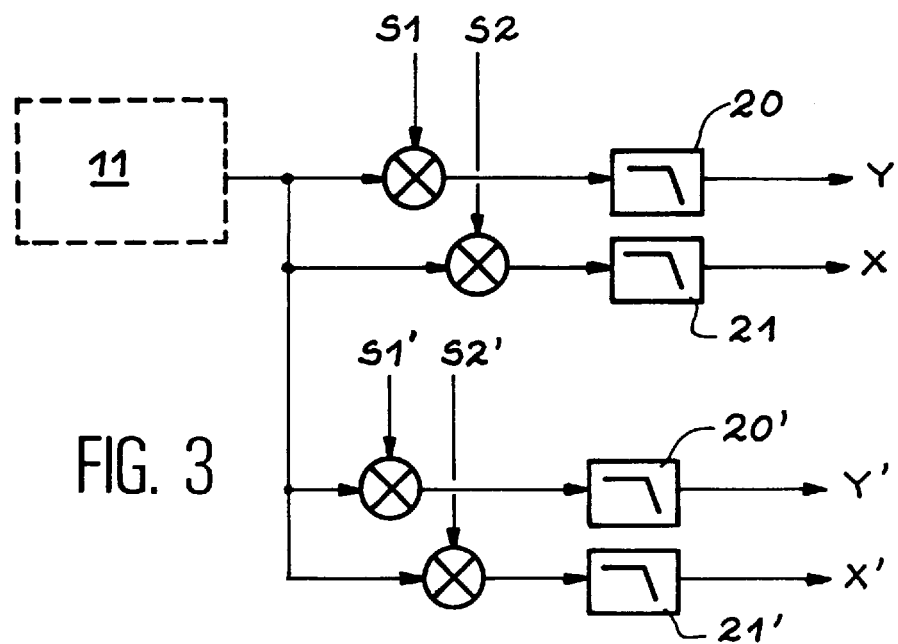
Figure 4:
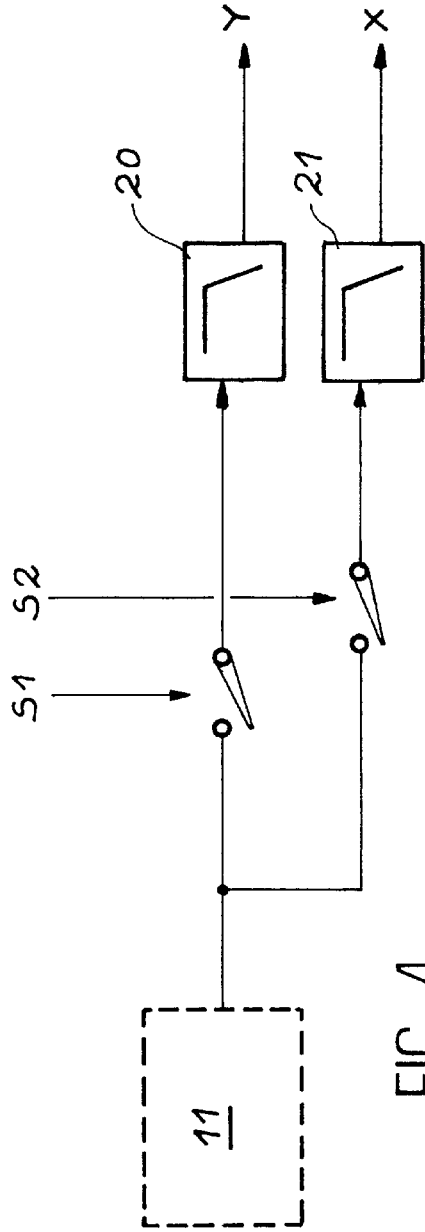
FIG. 4 illustrates a prior art, quadrature sampling demodulation device.

The originality of this method is based on the fact that the device of FIG. 5 is a demodulator of N simultaneous frequencies. There is no need to duplicate this diagram in order to demodulate more carriers. This demodulator can also be as insensitive to harmonics as that illustrated in FIG. 3. The quality of the demodulation is dependent on the algorithm used in the processor 27.

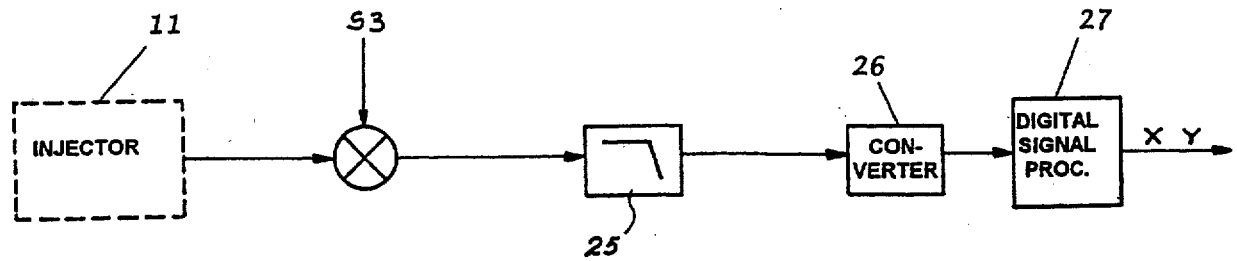

I claim:

1. Device for the simultaneous demodulation of a multi-frequency signal, comprising a processor, where the demodulation takes place by calculation, comprising an injector, whose output signal is multiplied by a complex signal in the following form:

$$S3 = a_1 \sin\{2\pi(f_1 + \varepsilon_1)t + \varphi_1\} + a_2 \sin\{2\pi(f_2 + \varepsilon_2)t + \varphi_2\} + \ldots a_n \sin\{2\pi(f_n + \varepsilon_n)t + \varphi_n\}$$

$\epsilon_1$ being a small frequency deviation and $\alpha_1$ a phase, the frequencies of the N sinusoids being the frequencies of the frequency-shifted carriers, so as to transpose the signal of the injection on the intermediate frequencies.

2. Device according to claim 1, comprising said injector followed by a multiplier and a low-pass filter, and said filter, having an antialiasing function, is followed by a digital converter.

3. Device according to claim 1, which is used for a measurement by eddy currents.

* * * * *

UNITED STATES PATENT AND TRADEMARK OFFICE
CERTIFICATE OF CORRECTION

PATENT NO. : 5,952,879
DATED : September 14, 1999
INVENTOR(S) : Edouard de Ledinghen It is certified that error appears in the above-identified patent and that said Letters Patent is hereby corrected as shown below:

Title page, should be deleted and substitute therefor the attached Title page.

Column 2, Line 26, delete "$\alpha_1$" and insert --$\varphi_1$--.

Column 4, Line 12, delete "$\alpha_1$" and insert --$\varphi_1$--.

The drawings (FIG. 1, FIG. 2, FIG. 3, FIG. 4, and FIG. 5) should be replaced with the attached drawings which include the descriptive legends.

Signed and Sealed this

Thirteenth Day of June, 2000

Attest:

Q. TODD DICKINSON

*Attesting Officer*   *Director of Patents and Trademarks*

United States Patent [19]
de Ledinghen

[11] Patent Number: 5,952,879
[45] Date of Patent: Sep. 14, 1999

[54] DEVICE FOR THE SIMULTANEOUS DEMODULATION OF A MULTIFREQUENCY SIGNAL, PARTICULARLY FOR AN EDDY CURRENT MEASUREMENT

[75] Inventor: Edouard de Ledinghen, Paris, France

[73] Assignee: Intercontrole, Rungis Cedex, France

[21] Appl. No.: 08/981,377

[22] PCT Filed: Jun. 19, 1996

[86] PCT No.: PCT/FR96/00947

§ 371 Date: Dec. 18, 1997

§ 102(e) Date: Dec. 18, 1997

[87] PCT Pub. No.: WO97/01217

PCT Pub. Date: Jan. 9, 1997

[30] Foreign Application Priority Data

Jun. 20, 1995 [FR] France .................. 9507357

[51] Int. Cl.$^6$ ............... H03D 3/00; H04L 27/22
[52] U.S. Cl. ............ 329/304; 329/306; 375/324; 375/329
[58] Field of Search ............... 329/304–310; 375/324, 325, 328, 329–333

[56] References Cited

U.S. PATENT DOCUMENTS

4,303,885 12/1981 Davis et al. .
4,467,281 8/1984 Davis et al. .
5,805,642 9/1998 Wei et al. ............... 329/304 X

FOREIGN PATENT DOCUMENTS

3435032 A1 4/1986 Germany .
WO 90/04292 4/1990 WIPO .

*Primary Examiner*—David Mis
*Attorney, Agent, or Firm*—Pearne, Gordon, McCoy & Granger LLP

[57] ABSTRACT

A device for the simultaneous demodulation of a multifrequency signal comprising a processor in which demodulation takes place by calculation. An injector's output signal is multiplied by a complex signal having sinusoids of varying frequencies corresponding to frequency-shifted carriers, thereby transposing the injector's signal on intermediate frequencies.

3 Claims, 2 Drawing Sheets